(12) United States Patent
Sugaya et al.

(10) Patent No.: US 6,883,371 B2
(45) Date of Patent: Apr. 26, 2005

(54) HUMIDITY SENSOR

(75) Inventors: Satoshi Sugaya, Aichi (JP); Tetsuo Yamada, Aichi (JP); Noboru Ishida, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 4 days.

(21) Appl. No.: 09/971,711

(22) Filed: Oct. 9, 2001

(65) Prior Publication Data

US 2002/0040598 A1 Apr. 11, 2002

(30) Foreign Application Priority Data

Oct. 10, 2000 (JP) .................................. 2000-309169

(51) Int. Cl.$^7$ .................................................. G01N 7/00
(52) U.S. Cl. ............................. 73/335.05; 73/335.05; 73/335.02; 73/335.03; 73/29.01; 73/29.05; 73/31.05; 73/23.31
(58) Field of Search ................... 73/335.05, 335.02, 73/29.01, 335.03, 29.05, 31.05, 23.31; 338/35

(56) References Cited

U.S. PATENT DOCUMENTS

| | | | | |
|---|---|---|---|---|
| 3,223,609 A | * | 12/1965 | Reeds, Jr. | 324/450 |
| 3,377,203 A | * | 4/1968 | Moibus et al. | 429/33 |
| 4,365,604 A | | 12/1982 | Sone | |
| 4,378,691 A | * | 4/1983 | Terada et al. | 73/31.06 |
| 4,379,406 A | * | 4/1983 | Bennewitz et al. | 73/335.02 |
| 4,602,426 A | * | 7/1986 | Kampe et al. | 29/623.1 |
| 4,608,232 A | * | 8/1986 | Sunano et al. | 73/31.05 |
| 4,656,455 A | * | 4/1987 | Tanino et al. | 73/29.05 |
| 4,713,166 A | * | 12/1987 | Kojima et al. | 204/425 |
| 4,954,238 A | * | 9/1990 | Kato et al. | 73/335.04 |
| 5,296,819 A | * | 3/1994 | Kuroiwa et al. | 73/335.02 |
| 5,369,995 A | * | 12/1994 | Scheinbeim et al. | 73/31.05 |
| 5,792,938 A | * | 8/1998 | Gokhfeld | 73/29.02 |
| 5,855,849 A | * | 1/1999 | Li et al. | 422/88 |
| 5,969,231 A | * | 10/1999 | Qu et al. | 204/425 |
| 5,993,625 A | * | 11/1999 | Inoue et al. | 204/425 |
| 6,126,312 A | * | 10/2000 | Sakai et al. | 374/28 |

FOREIGN PATENT DOCUMENTS

| | | | | |
|---|---|---|---|---|
| JP | 56089050 | | 7/1981 | |
| JP | 57039342 A | * | 3/1982 | .......... G01N/27/12 |
| JP | 63-163265 | | 7/1988 | |
| JP | 1-121745 | | 5/1989 | |
| JP | 1-196559 | | 8/1989 | |
| JP | 4-250351 | | 9/1992 | .......... G01N/27/22 |
| JP | 4-357447 | | 12/1992 | |
| JP | 6-118044 | | 4/1994 | .......... G01N/27/12 |
| JP | 2707246 | | 10/1997 | ............ H01C/7/00 |
| JP | 3074968 | | 6/2000 | |
| JP | 3174150 | | 3/2001 | .......... G01N/27/12 |
| WO | WO 00/28311 | | 5/2000 | |

OTHER PUBLICATIONS

European Search Report for EP 01 30 0624 dated Feb. 4, 2002.

* cited by examiner

Primary Examiner—Hezron Williams
Assistant Examiner—André K. Jackson
(74) Attorney, Agent, or Firm—Sughrue Mion, PLLC

(57) ABSTRACT

A humidity sensor including an insulating substrate, and a lower electrode formed from a noble metal, a moisture sensitive layer formed of a porous body predominantly containing alumina and containing predetermined amounts of $TiO_2$ and $SnO_2$ and an upper electrode formed of a noble metal porous body successively formed on the insulating substrate. The upper electrode is connected to the moisture sensitive layer and a portion of the insulating substrate. Preferably, the lower electrode is formed of a porous body. More preferably, the lower and upper electrodes are formed from Pt. Furthermore, preferably, a heater and a temperature measurement resistor are provided in the insulating substrate and are located directly below the moisture sensitive layer.

8 Claims, 5 Drawing Sheets

HUMIDITY SENSOR

BACKGROUND OF THE INVENTION

1. Field of the Invention

The present invention relates to a humidity sensor for measuring the moisture content of an atmosphere by means of change in the electrical resistance of a moisture sensitive layer. The humidity sensor can be used, for example, for measuring the moisture content of air; the moisture content of exhaust gas of an internal combustion engine of, for example, an automobile, ship, or airplane, particularly the moisture content of an atmosphere containing substantially no oxygen and containing a reducing gas; or the moisture content of a highly reducing atmosphere surrounding a fuel electrode or an air electrode of a fuel cell.

2. Description of the Related Art

Commercially available humidity sensors include resistance-variable-type humidity sensors utilizing adsorption and desorption of water molecules; and capacitance-variable-type humidity sensors utilizing a change in capacitance. Such humidity sensors are formed, for example, from a moisture sensitive ceramic material such as $Al_2O_3$, $MgCr_2O_4$—$TiO_2$, $TiO_2$—$V_2O_5$, or $ZrCr_2O_4$—$LiZrVO_4$. Most of the humidity sensors measure moisture content by means of a change in electric resistance.

A typical humidity sensor formed from such a moisture sensitive ceramic material includes an insulating substrate, a lower electrode formed on the substrate, a moisture sensitive layer provided on the lower electrode, and an upper electrode formed on the moisture sensitive layer. In many cases, the lower and upper electrodes are formed from a porous body of $RuO_2$ in order to enhance the strength of adhesion between the insulating substrate and the moisture sensitive layer, and to cause water vapor contained in air to easily pass through the moisture sensitive layer easily.

3. Problems Solved by the Invention

When an electrode formed from $RuO_2$ is exposed to a reducing atmosphere in an exhaust pipe of an automobile or in a specific portion of a fuel cell where the oxygen content is very low and temperature changes over a wide range (e.g., −40° C. to 750° C.), the electrode may be impaired with the passage of time. The problem then arises that the humidity sensor cannot detect a change in the resistance of the moisture sensitive material even though the humidity changes.

SUMMARY OF THE INVENTION

The present invention contemplates solving the aforementioned conventional problems of the prior art. It is therefore an object of the present invention to provide a humidity sensor of very high accuracy, which can maintain stable humidity detection performance over a long period of time even when the sensor is exposed to an atmosphere containing a very small amount of oxygen and a considerable amount of a reducing gas, such as the atmosphere in the exhaust pipe of an automobile.

The present inventors discovered that when lower and upper electrodes of a humidity sensor are formed from a noble metal exhibiting excellent heat resistance and corrosion resistance, such as platinum or gold, and the upper electrode is joined to a moisture sensitive layer and an electric insulating substrate, the moisture sensitive layer and the substrate can satisfactorily adhere to each other. A humidity sensor having this configuration exhibits enhanced durability, and can maintain excellent humidity detection performance over a long period of time. This is the case even when the sensor is exposed to an atmosphere which undergoes a drastic change in temperature and contains a very small amount of oxygen and a considerable amount of a reducing gas, such as the atmosphere in an exhaust pipe of an automobile; or even when the sensor is provided, for example, in a fuel or air feeding line of a fuel cell.

The present invention has been accomplished on the basis of this finding.

In a first embodiment of the invention, the humidity sensor comprises an insulating substrate, and a lower electrode, a moisture sensitive layer and an upper electrode successively formed on the insulating substrate, wherein the lower electrode comprises a noble metal, the upper electrode comprises a noble metal porous body, and the upper electrode is joined to the moisture sensitive layer and a portion of the insulating substrate.

The aforementioned "insulating substrate" may comprise a ceramic material such as $Al_2O_3$ or $ZrO_2$. Of these ceramic materials, alumina, which exhibits an excellent insulating property and mechanical strength and is advantageous in terms of cost, is widely employed. No particular limitation is imposed on the thickness and dimensions of the insulating substrate, but typically, the substrate is formed into a rectangular plate-like body having a thickness of 0.3–2.0 mm, and planar dimensions (width and length) of 3×10 mm to 8×50 mm.

The aforementioned "lower electrode" and "upper electrode" comprise at least one noble metal selected from among Au, Ag, Ru, Rh, Pd, Os, Ir and Pt. The electrodes may be formed from an alloy containing two or more of these noble metals. For example, a combination of Pt and Rh is useful, since evaporation of Pt at high temperature is suppressed. The lower electrode and the upper electrode are not necessarily formed from the same noble metal, but the electrodes are preferably formed from the same noble metal. This is because the process for forming the electrodes can be simplified and simultaneous firing of the electrodes can be carried out easily. Of these noble metals, Au or Pt is preferred. Particularly preferably, as described in a second embodiment of the invention, either or both of the electrodes predominantly contains Pt in an amount of 80% or more by weight. Pt does not easily oxidize at high temperature, does not diffuse in the moisture sensitive layer, and has a sufficiently high melting point. Therefore, when the lower and upper electrodes are formed from Pt, the humidity sensor exhibits further enhanced durability. The electrodes formed from the aforementioned noble metal may contain other components or impurities, so long as such "other components or impurities" do not greatly affect the properties of the electrodes.

Since the upper electrode is formed of a noble metal porous body, moisture can easily penetrate the upper electrode and reach the moisture sensitive layer. Therefore, absorption and desorption of water molecules smoothly proceed at the moisture sensitive layer. In order to promote absorption and desorption of water molecules at the moisture sensitive layer, moisture preferably reaches the entirety of the surface of the moisture sensitive layer. Therefore, as described in a third embodiment of the invention, preferably, not only the upper electrode but also the lower electrode comprises a porous body. When the moisture penetrability of the upper and lower electrodes is higher than that of the moisture sensitive layer, which is also formed of a porous body, moisture easily reaches the moisture sensitive layer.

Thus, in general, in order to facilitate moisture penetration through the electrodes, the pores in the upper and lower electrodes are made larger than those in the moisture sensitive layer. The size of pores in the upper and lower electrodes is preferably 0.5–20 μm, and the size of pores in the moisture sensitive layer is preferably 0.05–0.1 μm. In order to form the upper and lower electrodes exhibiting preferable moisture penetrability and conductivity, particles of ceramic such as alumina or zirconia are preferably incorporated, in an amount of 1–20 wt. %, into the upper and lower electrodes. The ceramic particle content is preferably at least 1 wt. % to effectively improve the moisture permeability of the electrodes. In contrast, the ceramic particle content is preferably 20 wt. % or less to reliably prevent poor electrode conductivity.

The aforementioned "moisture sensitive layer" may be formed from a variety of moisture sensitive materials. Examples of the moisture sensitive materials include moisture sensitive ceramic materials, such as $Al_2O_3$, $Al_2O_3$—$TiO_2$—$SnO_2$, $MgCr_2O_4$—$TiO_2$, $TiO_2$—$V_2O_5$, $ZrCr_2O_4$—$LiZrVO_4$, $ZnCrO_4$, $TiO_2$—$SnO_2$, and NASICON (Na-Super Ionic Conductor). When the moisture sensitive layer is formed from a moisture sensitive material containing a plurality of oxides, the proportions of the oxides are not particularly limited; i.e., the moisture sensitive layer may be formed from a generally used moisture sensitive material.

The humidity sensor as described in the first embodiment of the inventions including the insulating substrate, the lower electrode, the moisture sensitive layer, and the upper electrode, can be used in practice by connecting lead wires to and extending from the upper and lower electrodes, in order to obtain an output from the sensor. However, as described in a fourth embodiment of the invention, preferably, the humidity sensor comprises a heater provided in the insulating substrate. When the humidity sensor is periodically heated by means of the heater, moisture and other impurities that have invaded the moisture sensitive layer can be completely removed. Through this removal, the moisture sensitive layer is always maintained in a clean state, detection accuracy is enhanced, and the sensor maintains excellent detection characteristics over a long period of time. Even when the humidity is very high, dew condensation onto the sensor can be prevented by operating the heater.

In the humidity sensor which measures moisture content on the basis of change in the resistance of the moisture sensitive layer, the resistance of the moisture sensitive layer changes in accordance with the temperature of an atmosphere under detection; i.e., the resistance of the layer has temperature dependency. Therefore, as described in a fifth embodiment of the invention, the humidity sensor preferably comprises a temperature measurement resistor provided within the insulating substrate. Change in the resistance of the moisture sensitive layer with temperature is corrected by the temperature measurement resistor, and thus humidity can be detected at high accuracy independent of the temperature of the atmosphere. In addition to the ability of the moisture sensitive layer to measure the relative humidity of the atmosphere, the temperature measurement resistor can measure the temperature of the atmosphere. As a result, the absolute humidity of the atmosphere can also be measured.

As described in a sixth embodiment of the invention, preferably, the heater and the temperature measurement resistor provided in the insulating substrate are located directly below the moisture sensitive layer. When the heater is provided directly below the moisture sensitive layer, the entire moisture sensitive layer is easily heated in a substantially uniform manner, moisture and other impurities that have invaded the moisture sensitive layer can be removed efficiently, and the power consumption required for heating the layer can be reduced to the greatest possible extent. Meanwhile, by providing the temperature measurement resistor directly below the moisture sensitive layer, the temperature of the atmosphere can be measured at a position which is substantially the same as the position at which the humidity is detected, without being affected by heat conduction of the insulating substrate. Therefore, accuracy in humidity detection can be further enhanced.

When the humidity sensor as described in the first embodiment has a specific structure as described in any of the second through sixth embodiments, even when the sensor is used in an atmosphere as defined in a seventh embodiment; i.e., an atmosphere containing a very small amount of oxygen and containing a reducing gas, the sensor maintains excellent detection performance over a long period of time. Therefore, the sensor is particularly useful for measuring the moisture content of a specific atmosphere in an exhaust pipe of an automobile or in a fuel cell. The expression "the amount of oxygen is very small" means an amount of oxygen as measured by a conventional apparatus at the detection limit or less; for example, an amount of about $10^{-9}$ to $10^{-20}$ atm. The expression "an atmosphere containing reducing gas" means an atmosphere containing a reducing gas (e.g., HC, CO, NO, $H_2$) in a certain amount or more such that the reducing gas can bring about chemical equilibrium (e.g., CO=3144 ppm, THC-total hydrocarbon ($CH_4$, $C_3H_6$, $C_7H_8$, etc.)=459 ppm, NO=243 ppm).

BRIEF DESCRIPTION OF THE DRAWINGS

FIG. 1(*b*) is a cross-sectional view of the humidity sensor taken along line A–A' of FIG. 1(*a*).

DESCRIPTION OF REFERENCE NUMERALS USED IN THE DRAWINGS

Figure 1:
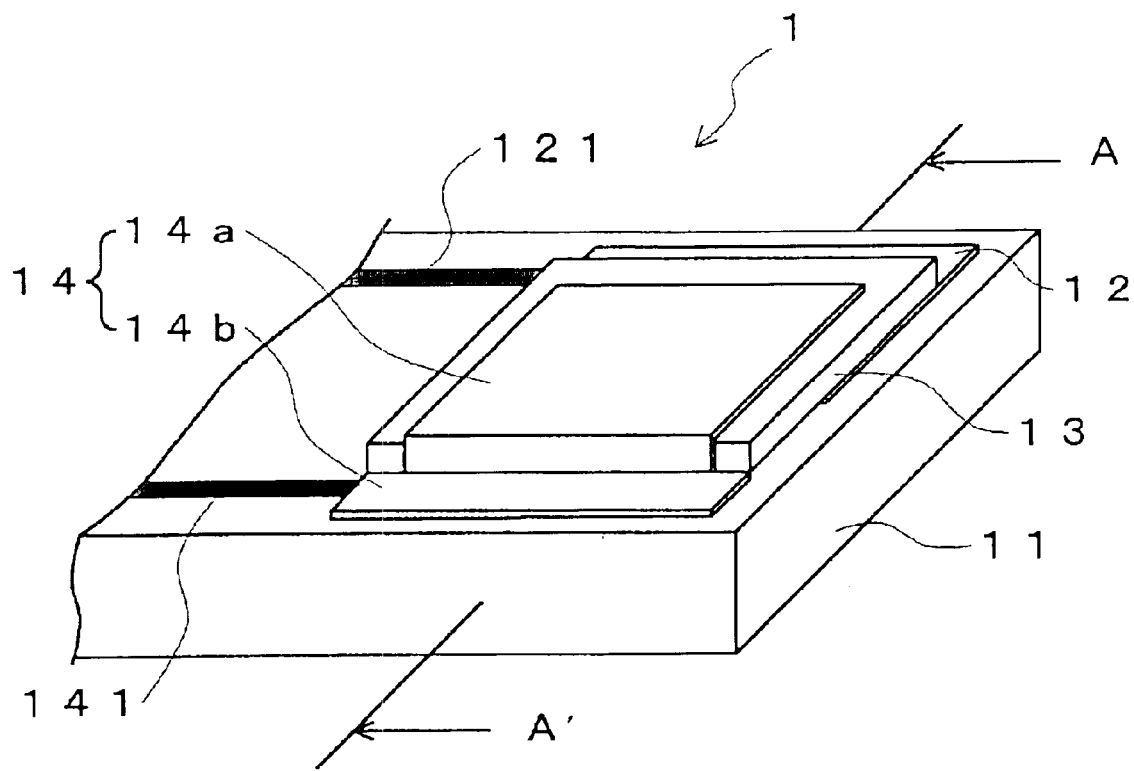
FIG. 1(*a*) is a schematic perspective view of a humidity sensor.

1: humidity sensor
11: insulating substrate
111: heater
112: temperature measurement resistor
12: lower electrode
13: moisture sensitive layer
14: upper electrode
14*a*: a portion of upper electrode
14*b*: other portion of upper electrode
121, 141: output lead wires connected to electrodes
2: air cylinder 31: mass flow (wet)
32: mass flow (dry)
4: thermostatic chamber
51: first saturation bath
52: second saturation bath
6: evaluation container
7: temperature-humidity detection apparatus

DETAILED DESCRIPTION OF THE PREFERRED EMBODIMENTS

The present invention will next be described in more detail by way of example. However, the present invention should be construed as being limited thereto.

(1) Structure of Humidity Sensor

Figure 1B:
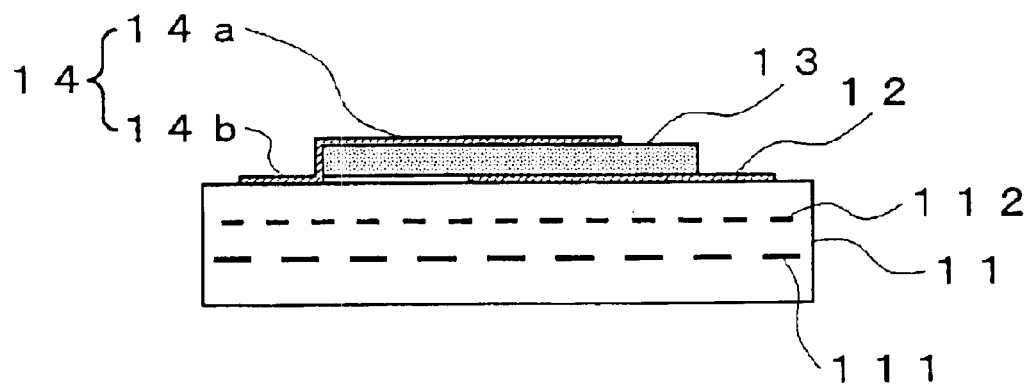

FIG. 1(a) is a perspective view showing an essential portion of a humidity sensor according to one embodiment of the present invention. FIG. 1(b) is a cross-sectional view of the humidity sensor taken along line A–A' in FIG. 1(a).

(i) Insulating Substrate

An insulating substrate 11 is formed from $Al_2O_3$, and has a thickness of 1.6 mm, a width of 4 mm, and a length of 45 mm. A heater 111 which is formed from Pt and assumes the shape of a bent strip is provided in the insulating substrate located directly below a moisture sensitive layer at a position which is about ¼ the thickness of the substrate distant from the lower surface of the substrate. A temperature measurement resistor 112 which is formed from Pt and assumes the shape of a bent strip is provided in the insulating substrate located directly below the moisture sensitive layer at a position which is about ¼ the thickness of the substrate distant from the upper surface of the substrate.

(ii) Moisture Sensitive Layer, Electrodes, etc.

A lower electrode 12 formed from Pt is joined to the upper surface at one longitudinal end of the insulating substrate. The lower electrode 12 is formed of a porous body having pores of 0.5–10 μm and contains 12 wt. % $Al_2O_3$. The lower electrode 12 has a thickness of 30 μm, a width of 2 mm, and a length of 2.5 mm. The lower surface of a moisture sensitive layer 13 formed from a moisture sensitive ceramic material containing $Al_2O_3$ and predetermined amounts of $TiO_2$ and $SnO_2$ is joined to the entire surface of the lower electrode and a portion of the insulating substrate. The moisture sensitive layer 13 is formed of a porous body having pores of 0.05–0.2 μm. The moisture sensitive layer 13 has a thickness of 400 μm, a width of 2.5 mm, and a length of 2.5 mm. An upper electrode 14 formed from Pt is joined to the upper surface of the moisture sensitive layer which is opposite the lower electrode; one side end surface of the moisture sensitive layer; and a portion of the upper surface of the insulating substrate. The thickness of the upper electrode 14 is 30 μm. The upper electrode 14 is formed of a porous body having pores of 0.5–10 μm and containing 12 wt. % $Al_2O_3$. A portion 14a of the upper electrode 14 provided on the upper surface of the moisture sensitive layer has a width of 2 mm and a length of 2 mm. A portion 14b of the upper electrode 14 provided on the upper surface of the insulating substrate has a width of 0.5 mm and a length of 2.5 mm.

Output lead wires 121 and 141 are connected to the lower electrode and the upper electrode, respectively, and the lead wires extend from the electrodes. The heater is connected to a power supply source, and the temperature measurement resistor is connected to a temperature detection circuit. The power supply source, the temperature detection circuit, and lead wires connected thereto are not illustrated for the sake of simplicity.

(2) Production of Humidity Sensor (i) Production of an insulation substrate having output lead wires thereon, and a heater and a temperature measurement resistor disposed within the substrate.

A slurry containing alumina powder was prepared, and alumina green sheets A, B, C and D (the entirety to serve as an insulating substrate 11 after firing) (thickness of each sheet: 450 μm) were formed from the slurry using a doctor blade process. Thereafter, through screen printing, a Pt-containing paste for a heater was applied onto the upper surface of the alumina green sheet A, to thereby form a heater pattern (to serve as a heater 111 and a wire to be connected to a power supply source (not illustrated) after firing).

Through screen printing, a Pt-containing paste for a temperature measurement resistor was applied onto a first surface of the alumina green sheet C, to thereby form a temperature measurement resistor pattern (to serve as a temperature measurement resistor 112 and a wire to be connected to a temperature detection circuit (not illustrated) after firing). Furthermore, through screen printing, a Pt-containing paste for an output lead wire was applied onto a first surface of the alumina green sheet D, to thereby form output lead wire patterns (to serve as output lead wires 121 and 141 after firing).

Subsequently, the alumina green sheets A to D were stacked on one another, such that 1) a second surface of the alumina green sheet D (the output lead wire patterns having been formed on the first surface thereof) came into contact with the first surface of the alumina green sheet C on which the temperature measurement resistor pattern had been formed; 2) a second surface of the alumina green sheet C came into contact with a first surface of the alumina green sheet B, the sheet B serving as an insulating layer for further securing contact between the heater pattern and the temperature measurement resistor pattern; and 3) a second surface of the alumina green sheet B came into contact with a first surface of the alumina green sheet A on which the heater pattern has been formed. The resultant product was pressed to thereby form a laminate. Thereafter, the resultant laminate was fired at 1,550° C. for two hours, to thereby produce an insulating substrate in which a heater and a temperature measurement resistor were provided.

The dimensions of the green sheets were determined such that 10 insulating substrates could be produced. Heater patterns, temperature measurement resistor patterns, and output lead wire patterns were formed in a number corresponding to the number of the substrates. The green sheets were stacked as described above, and the resultant laminate was cut into green substrates. The resultant green substrates were fired to thereby produce 10 insulating substrates simultaneously.

(ii) Production of Moisture Sensitive Layer

A powder mixture containing $Al_2O_3$ powder and predetermined amounts of $TiO_2$ powder and $SnO_2$ powder was formed into a predetermined shape. Thereafter, the resultant product was fired at 1,200° C. for two hours, to thereby produce a moisture sensitive layer having a thickness of 400 μm, a width of 2.5 mm, and a length of 2.5 mm.

(iii) Production of Humidity Sensor

On a first surface of the moisture sensitive layer produced in (ii) above, a portion of an upper electrode pattern (to serve as a portion 14a of an upper electrode after firing) was printed using a platinum paste, and then dried, to thereby form a film having a thickness of 30 μm, a width of 2 mm, and a length of 2 mm. Thereafter, a lower electrode pattern (to serve as a lower electrode 12 after firing) was printed, using a platinum paste, on the upper surface of the insulating substrate produced in (i) above (the temperature measurement resistor is provided in the vicinity of the surface) at one longitudinal end of the substrate, and then dried, to thereby form a film having a thickness of 30 μm, a width of 2 mm, and a length of 2.5 mm. Subsequently, the moisture sensitive layer was pressed onto the insulating substrate such that the lower surface of the moisture sensitive layer came into contact with the entire surface of the film and a portion of the upper surface of the substrate. Thereafter, in order to cause the moisture sensitive layer and the insulating substrate to adhere to each other sufficiently, and to secure conduction between an upper electrode 14 and an output lead wire 141, another portion of the upper electrode pattern (to serve as another portion 14b of the upper electrode after firing) was printed on one side end of the moisture sensitive layer and on a portion of the upper surface of the insulating substrate, such that the other portion was connected to the aforementioned portion of the upper electrode pattern, and then dried, to thereby form a film having a thickness of 30 μm, a width of 0.5 mm, and a length of 2.5 mm.

Thereafter, the resultant laminate including the insulating substrate, the lower electrode pattern, the moisture sensitive layer, and the upper electrode pattern was fired at 1,200° C. for 10 minutes, to thereby produce a humidity sensor.

Figure 2:
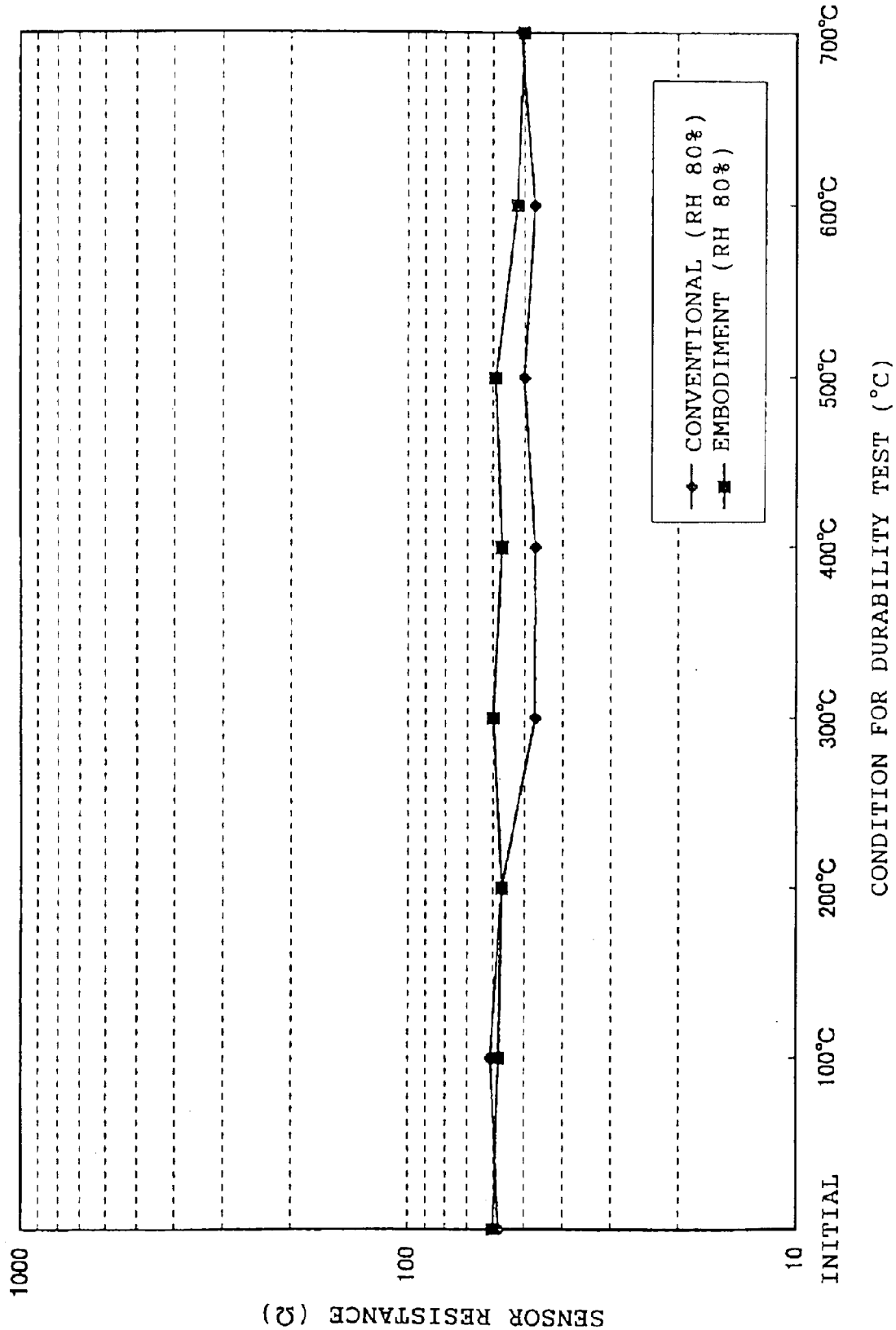
FIG. 2 is a graph showing a comparison in durability between the humidity sensor of the present invention and a conventional humidity sensor when these sensors are exposed to an atmosphere containing a large amount of oxygen and a very small amount of a reducing gas.

(3) Evaluation of Durability of Humidity Sensor (i) Evaluation in an Atmosphere containing a Large Amount of Oxygen and a Very Small Amount of a Reducing Gas The humidity sensor produced in (2), and a conventional humidity sensor in which lower and upper electrodes are formed from $RuO_2$ instead of Pt were exposed for 30 minutes, in an exhaust pipe of a diesel automobile, to exhaust gas containing a large amount of oxygen and a very small amount of reducing gas, and these sensors were evaluated in terms of time-course change in humidity detection characteristics. The temperature of the exhaust gas was changed from 100 to 700° C. at intervals of 100° C., and the change in characteristics with respect to temperature was also evaluated. FIG. 2 shows the results when the sensors were evaluated by means of a shunting method at a relative humidity of 80%.

Composition of exhaust gas: $O_2$ (16%), $CO_2$ (3%), $H_2O$ (3%), other gasses (HC, NO, CO, etc.) (very small amounts, e.g., 500 ppm or less).

Evaluation method: After the humidity sensor was exposed to the exhaust gas of an actual automobile at the aforementioned temperatures, the detection characteristics of the sensor were measured by means of a shunting method (JIS Z 8806-1981), and the time-course change of the sensor with respect to the exhaust gas and the temperature thereof was evaluated.

Evaluation conditions: measurement temperature (20° C.), evaluation gas (air), relative humidity (40%, 60%, 80%, or 90%).

Figure 5:
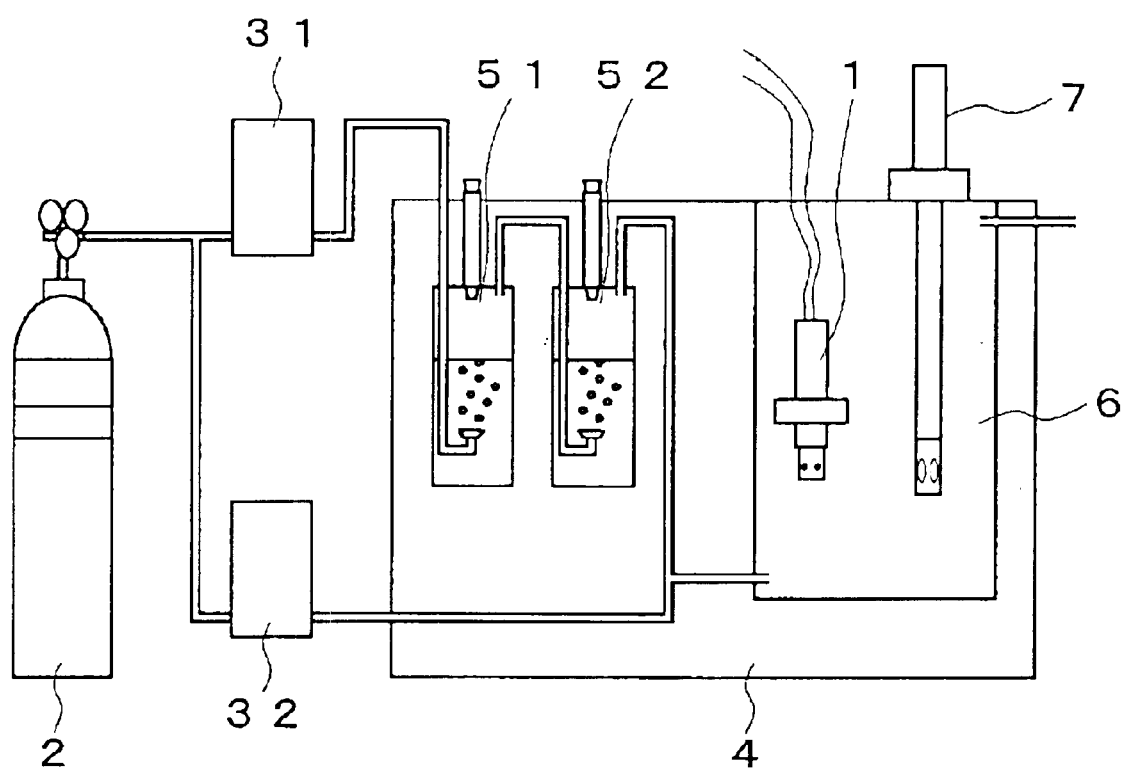
FIG. 5 is a schematic representation showing an apparatus for evaluating detection characteristics of a humidity sensor by means of a shunting method.

In this embodiment, as shown in FIG. 5, evaluation gas is supplied through each line from air cylinder 2. Adjusting the volume of the evaluation gas in mass flow (dry) 32 and in mass flow (wet) 31 to predetermined values, evaluation gas is supplied through thermostatic chamber 4 into evaluation container 6 in which the resistance changing characteristics of the humidity sensor 1 with respect to a change in humidity is measured. Additionally the predetermined values of the evaluation gas supplied to the evaluation container 6 is confirmed by a temperature-humidity detection apparatus 7.

The thermostatic chamber 4 is adjusted to 20° C. and the total flow rate of the mass flow 31, 32 is adjusted to 5 liters/min. Further, the first saturation bath 51 and the second saturation bath 52 are each provided in a wet line between the mass flow wet 31 and the evaluation container 6 so as to saturate the evaluation gas.

As shown in FIG. 2, the humidity sensor produced in (2) in which the upper and lower electrodes are formed from Pt exhibited no significant difference from the conventional humidity sensor having a structure similar to that of the above humidity sensor except that the upper and lower electrodes are formed from $RuO_2$, in that the detection characteristics do not vary regardless of exposure to the exhaust gas or variation in the temperature of the exhaust gas. Therefore, when being exposed to an atmosphere containing a large amount of oxygen and a very small amount of reducing gas, $RuO_2$ as well as Pt effectively functions as an electrode of the humidity sensor.

Figure 3:
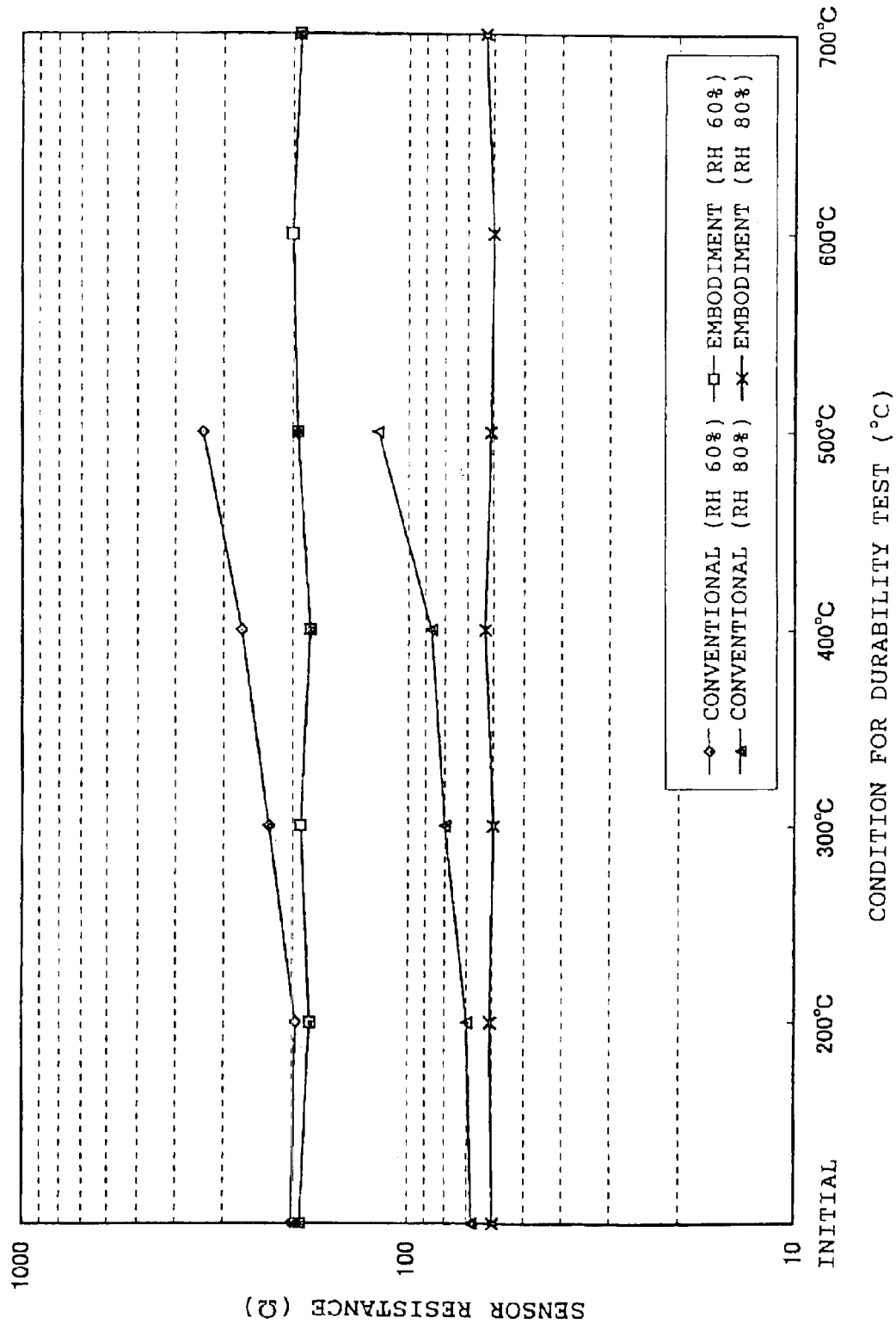
FIG. 3 is a graph showing a comparison in durability between the humidity sensor of the present invention and a conventional humidity sensor when these sensors are exposed to an atmosphere containing substantially no oxygen and containing a large amount of a reducing gas.

(ii) Evaluation in an Atmosphere Containing Substantially No Oxygen and Containing a Large Amount of a Reducing Gas The humidity sensor produced in (2) and a conventional humidity sensor in which lower and upper electrodes are formed from $RuO_2$ instead of Pt were exposed for 30 minutes, in an exhaust pipe of a gasoline automobile engine (air-fuel ratio was regulated to 14.0), to exhaust gas containing substantially no oxygen and containing a large amount of a reducing gas, and these sensors were evaluated in terms of the time-course change in humidity detection characteristics. The temperature of the exhaust gas was changed from 200 to 700° C. at intervals of 100° C., and the change in characteristics with respect to temperature was also evaluated. FIG. 3 shows the results when the sensors were evaluated by means of a shunting method at relative humidities of 60% and 80%.

Composition of exhaust gas: $O_2$ (substantially not present), $CO_2$ (10%), $H_2O$ (10%), other gasses (HC, NO, CO, etc.) (very small amounts, e.g., 500 ppm or less).

Evaluation method and evaluation conditions were similar to those in the case of (i).

Figure 4:
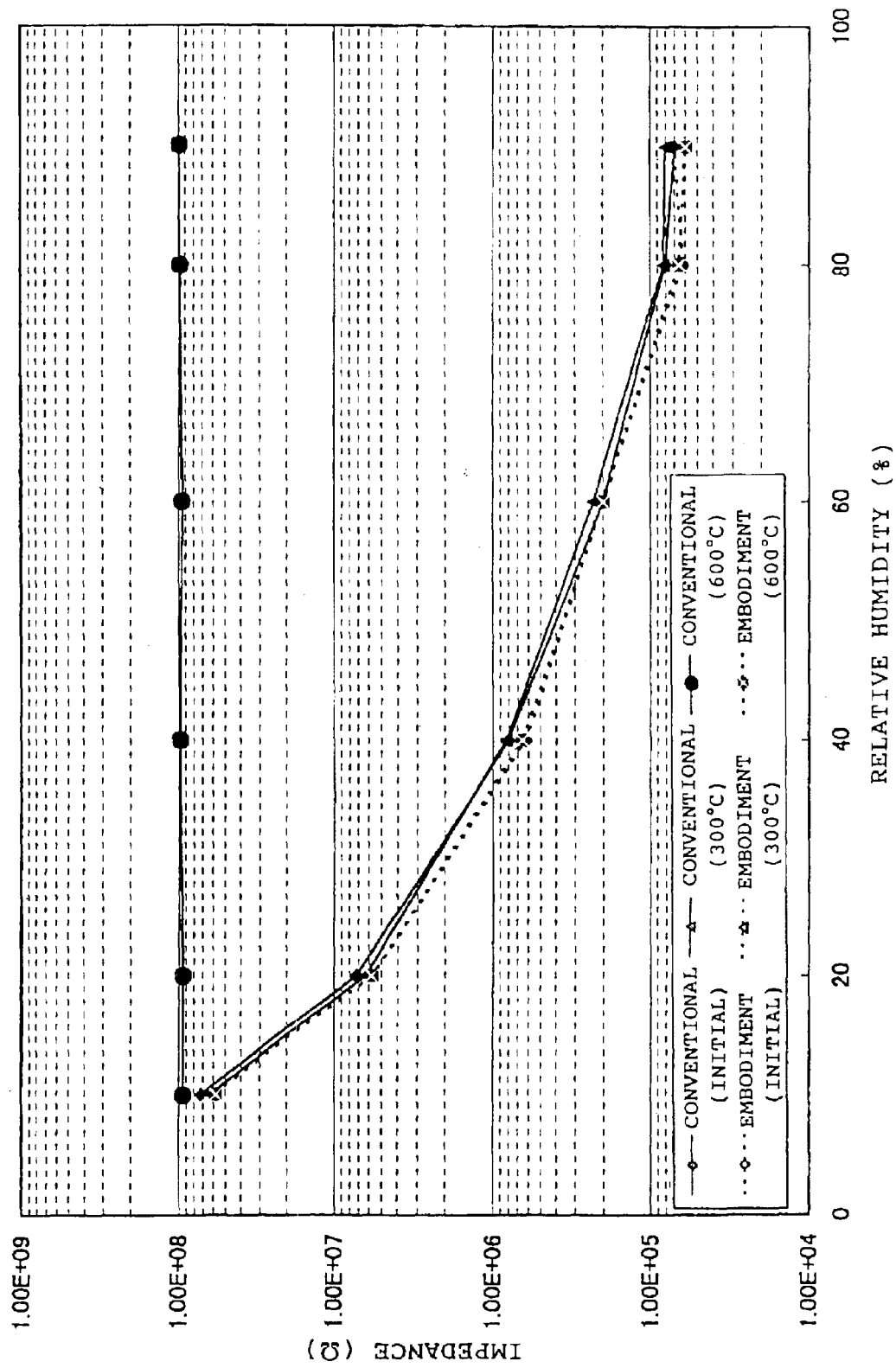
FIG. 4 is a graph showing a comparison in output impedance between the humidity sensor of the present invention and a conventional humidity sensor when relative humidity is changed.

As shown in FIG. 3, in the case of the humidity sensor produced in (2) in which the upper and lower electrodes are formed from Pt, detection characteristics do not vary, regardless of exposure to the exhaust gas or variation in the temperature of the exhaust gas. Therefore, even when the humidity sensor is exposed to an atmosphere which undergoes a drastic change in temperature, or to an atmosphere containing a very small amount of oxygen and a large amount of a reducing gas, the humidity sensor does not lose its function as a humidity sensor and exhibits excellent durability. In contrast, in the case of the conventional humidity sensor in which the upper and lower electrodes are formed from $RuO_2$, the resistance substantially increases when the temperature of the exhaust gas is approximately 400–500° C. As shown in FIG. 4, when the temperature of the exhaust gas is 600° C. or higher, the impedance of the conventional humidity sensor becomes approximately 1.00E+08 Ω, regardless of the relative humidity; i.e., the sensor does not function as a humidity sensor.

EFFECTS OF THE INVENTION

The first embodiment of the invention provides a humidity sensor of high accuracy exhibiting excellent durability, in which the strength of adhesion between an insulating substrate and a moisture sensitive layer is enhanced. Particularly, when the humidity sensor has a specific structure as described in the second through sixth embodiments, even if the sensor is used in a specific atmosphere as described in the seventh embodiment, the sensor exhibits high accuracy and excellent durability.

It should further be apparent to those skilled in the art that various changes in form and detail of the invention as shown and described above may be made. It is intended that such changes be included within the spirit and scope of the claims appended hereto.

This application is based on Japanese Patent Application No. 2000-309169 filed Oct. 10, 2000, the disclosure of which is incorporated herein by reference in its entirety.

What is claimed is:

1. A humidity sensor for measuring the humidity of an atmosphere to which the humidity sensor is exposed comprising:

an insulating substrate; and a lower electrode, a moisture sensitive layer and an upper electrode successively formed on the insulating substrate, said moisture sensitive layer having an electrical resistance which changes with a change in humidity and said humidity sensor providing a measurement of humidity based on the electrical resistance of said moisture sensitive layer, wherein the lower electrode comprises a noble metal porous body, the upper electrode comprises a noble metal porous body, the moisture sensitive layer is porous, and the upper electrode is joined to the moisture sensitive layer and a portion of the insulating substrate, and wherein a size of pores in the upper electrode is 0.5–20 $\mu$m, a size of pores in the lower electrode is 0.5–20 $\mu$m, a size of pores in the moisture sensitive layer is 0.05–0.2 $\mu$m, particles of ceramic are incorporated in an amount of 1–20 wt % into the upper electrode, particles of ceramic are incorporated in an amount of 1–20 wt % into the lower electrode, and one or both of the lower electrode and the upper electrode predominantly contains Pt.

2. The humidity sensor as claimed in claim 1, further comprising a heater provided in the insulating substrate.

3. The humidity sensor as claimed in claim 2, comprising a temperature measurement resistor provided in the insulating substrate.

4. The humidity sensor as claimed in claim 2, wherein the heater is located directly below the moisture sensitive layer.

5. The humidity sensor as claimed in claim 3, wherein the temperature measurement resistor is located directly below the moisture sensitive layer.

6. The humidity sensor as claimed in claim 1, adapted for measuring humidity in an atmosphere containing a very small amount of oxygen and containing a reducing gas.

7. The humidity sensor as claimed in claim 1, wherein one or both of the lower electrode and the upper electrode predominantly contains Pt and further contains Rh.

8. The humidity sensor as claimed in claim 1, wherein each of the lower electrode and the upper electrode predominantly contains Pt and further contains Rh.

* * * * *